United States Patent
Godek et al.

(10) Patent No.: US 9,517,232 B2
(45) Date of Patent: *Dec. 13, 2016

(54) COMPOUNDS FOR TREATMENT OF ALZHEIMER'S DISEASE

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: Medi Synergics, LLC, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/854,928

(22) Filed: Sep. 15, 2015

(65) Prior Publication Data

US 2016/0158209 A1 Jun. 9, 2016

Related U.S. Application Data

(63) Continuation-in-part of application No. 14/523,278, filed on Oct. 24, 2014, now Pat. No. 9,169,237.

(60) Provisional application No. 61/899,181, filed on Nov. 2, 2013.

(51) Int. Cl.
| | |
|---|---|
| *A61K 31/44* | (2006.01) |
| *A61K 31/443* | (2006.01) |
| *A61K 31/343* | (2006.01) |
| *A61K 45/06* | (2006.01) |
| *A61K 31/155* | (2006.01) |
| *A61K 31/4025* | (2006.01) |
| *A61K 31/404* | (2006.01) |
| *A61K 31/4192* | (2006.01) |
| *A61K 31/4709* | (2006.01) |
| *A61K 31/4965* | (2006.01) |
| *A61K 31/5377* | (2006.01) |
| *A61K 31/541* | (2006.01) |
| *A61K 31/55* | (2006.01) |
| *C07D 405/12* | (2006.01) |
| *C07D 307/78* | (2006.01) |
| *C07D 307/87* | (2006.01) |

(52) U.S. Cl.
CPC .......... *A61K 31/443* (2013.01); *A61K 31/155* (2013.01); *A61K 31/343* (2013.01); *A61K 31/404* (2013.01); *A61K 31/4025* (2013.01); *A61K 31/4192* (2013.01); *A61K 31/4709* (2013.01); *A61K 31/4965* (2013.01); *A61K 31/5377* (2013.01); *A61K 31/541* (2013.01); *A61K 31/55* (2013.01); *A61K 45/06* (2013.01); *C07D 307/78* (2013.01); *C07D 307/87* (2013.01); *C07D 405/12* (2013.01)

(58) Field of Classification Search
CPC ........................... A61K 31/443; A61K 31/343
USPC .................................................. 514/469, 337
See application file for complete search history.

(56) References Cited

U.S. PATENT DOCUMENTS 9,169,237 B1 * 10/2015 Godek ................ A61K 31/443
2014/0296211 A1 10/2014 Vamvakides et al.

OTHER PUBLICATIONS

Nguyen L, Lucke-Wold BP, Mookerjee SA, et al; "Role of sigma-1 receptors in neurodegenerative diseases." (2015) J. Pharmacological Sciences, 127:17-29.
Ruscher K, Shamloo M, Rickhag M, et al; "The sigma-1 receptor enhances brain plasticity and funtional recovery after experimental stroke." (2011) Brain, p. 1-15.
Francardo V, Bez F, Wieloch T, et al; "Pharmacological stimulation of sigma-1 receptors has neurorestorative effects in experimental parkinsonism." (2014) Brain 1-17.
Mavlyutov TA, Gup L-W, Epstein ML, Ruoho AE; "Role of the Sigma-1 receptor in Amytrophic Lateral Sclerosis (ALS)." (2015) J. Pharmacological Sciences, 127(1): 10-16.
Lahmy V, Meunier J, Malmstrom S, et al; "Blockade of Tau Hyperphosphorylation and Ab1-42 Generation" (2013) Neuropsychopharmacology, 38:1706-23.
Voges O, et al "A Phase 1 Dose Escalation Study to Investigate Safety, Tolerability, and Pharmacokinetics of ANAVEX 2-73" (2014) Poster, CNS Summit 2014, Boca Raton, FL.
Villard V, Espallergues J, Keller E, Anti-amnesic and neuroprotective potentials of the mixed muscarinic receptor/sigma 1 ligand ANAVEX 2-73, J Psychopharmacol. (Sep. 9, 2010).

* cited by examiner

*Primary Examiner* — Shengjun Wang

(57) ABSTRACT

The invention is directed to the use of a compound of formula I, as defined herein, to a pharmaceutically acceptable salt thereof; to a pharmaceutical composition containing a compound of formula I, and to a combination of a compound of formula I with a pharmacologically effective cholinesterase inhibitor to treat a mammal, including a human, for a disorder or condition selected from the list including Alzheimer's disease, Huntington's disease, Parkinson's disease, non-Alzheimer's dementias and ALS.

1 Claim, No Drawings

COMPOUNDS FOR TREATMENT OF ALZHEIMER'S DISEASE

This application claims the benefit of U.S. Provisional application Ser. No. 61/899,181 filed on Nov. 2, 2013.

BACKGROUND OF THE INVENTION

This invention is directed to compounds of the formula I described herein, to a pharmaceutical composition comprising such compounds and to methods of treating disorders or conditions that may be treated by administration of such compounds to a mammal in need, including humans. In particular, the compounds of the current invention are potentially useful for treating Alzheimer's disease and other dementias.

Alzheimer's disease is the most common form of dementia, producing memory loss and other intellectual disabilities serious enough to interfere with normal daily routine. It accounts for 60 to 80 percent of dementia cases. The majority of people with Alzheimer's are 65 and older; however, up to 5 percent of people with the disease have early onset Alzheimer's in their 40's or 50's. In 2010, there were between 21 and 35 million people worldwide with AD. In 2010, dementia was attributed to about 486,000 deaths in the U.S.

Alzheimer's is a progressive disease, where dementia symptoms gradually worsen over a number of years. In late-stage Alzheimer's, individuals lose the ability to carry on a conversation and respond to their environment. It is the sixth leading cause of death in the United States. Alzheimer's patients generally live an average of eight years after their symptoms become noticeable to others, but survival can range from four to 20 years, depending on age and other health conditions. Alzheimer's has no known cure and while current treatments don't stop Alzheimer's from progressing, they can temporarily slow the worsening of dementia symptoms and improve quality of life for those with Alzheimer's and their caregivers.

Alzheimer's disease (AD) is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Degeneration is also present in brainstem nuclei like the locus coeruleus. Studies using MRI and PET have documented reductions in the size of specific brain regions in people with AD as they progressed from mild cognitive impairment to Alzheimer's disease, and in comparison with similar images from healthy older adults.

Both amyloid plaques and neurofibrillary tangles are clearly visible by microscopy in brains of those afflicted by AD. Plaques are dense, mostly insoluble deposits of beta-amyloid peptide and cellular material outside and around neurons. Tangles (neurofibrillary tangles) are aggregates of the microtubule-associated protein tau which has become hyper-phosphorylated and accumulate inside the cells themselves. Although many older individuals develop some plaques and tangles as a consequence of ageing, the brains of people with AD have a greater number of them in specific brain regions such as the temporal lobe. Lewy bodies are not rare in the brains of people with AD.

The U.S. Food and Drug Administration (FDA) has approved a small number of cholinesterase inhibitors, including donepezil (Aricept™, the only cholinesterase inhibitor approved to treat all stages of Alzheimer's disease, including moderate to severe), rivastigmine (Exelon™, approved to treat mild to moderate Alzheimer's), galantamine (Razadyne™, mild to moderate patients) and memantine (Namenda™). Donepezil is the only cholinesterase inhibitor approved to treat all stages of Alzheimer's disease, including moderate to severe.

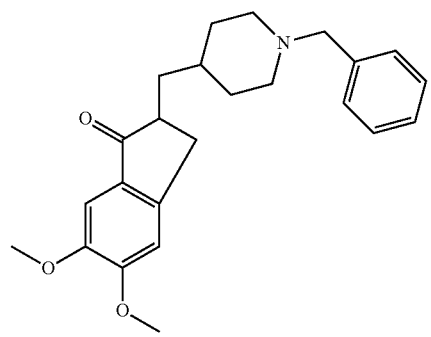

donepezil

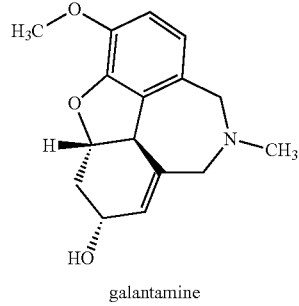

galantamine

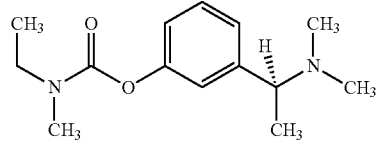

rivastigmine

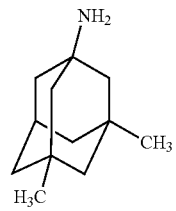

memantine

Memantine is prescribed to improve memory, attention, reason, language and the ability to perform simple tasks. It can be used alone or with other Alzheimer's disease treatments. There is some evidence that individuals with moderate to severe Alzheimer's who are taking a cholinesterase inhibitor might benefit by also taking memantine. It regulates the activity of glutamate, a different messenger chemical involved in learning and memory and it delays worsening of symptoms for some people temporarily. Many experts consider its benefits similar to those of cholinesterase inhibitors.

Recently, there has been increased awareness of the potential for compounds which function as sigma-1 receptor ligands. The structure and functions of the "receptor" have been described in a variety of publications (e.g., Duncan G and Wang L (2005) *Experimental Eye Research*, 81:121-122; Ortega-Roldan J L, Ossa F, Schnell J R (2013) *Journal* of Biological Chemistry, 288(29):21448-21457; Monnet F P (2005) Biol. Cell 97:873-883 (doi:10.1042/BC20040149); Ishikawa M, Hashimoto K (2010) Journal of Receptor, Ligand and Channel Research, 3:25-36)

In a paper by Nguyen, et al (Nguyen L, Lucke-Wold B P, Mookerjee S A Cavendish J Z, Robson M J, Scandinaro A L and Matsumoto R R, Journal of Pharmacological Sciences (2015) 127:17-29), the mechanisms of neurodegeneration, including Alzheimer's disease, and the potential for the use of highly selective sigma-1 receptor ligands is discussed in great detail. They describe the mechanisms by which drugs that interact with the sigma-1 receptor may provide neuroprotection, including calcium homeostasis, attenuation of reactive species (e.g., NO) production, modulation of endoplasmic reticulum (ER) and mitochondrial function and modulation of glial activity. Because of these capabilities, they postulate that sigma-1 ligands may have beneficial effects in the treatment of stroke, ALS and Huntington's diseases.

Anavex Life Sciences Corp. has recently begun Phase 2a clinical trials with ANAVEX 2-73, a compound which possesses mixed sigma-1 and muscarinic receptor affinities. The company claims that the drug has the potential to reduce protein misfolding in the brain, a hallmark of Alzheimer's disease, and has demonstrated improved cognitive function with mild to moderate AD patients. Furthermore, they claim a positive, synergistic response when patients were treated with ANAVEX 2-73 and the acetylcholinesterase inhibitor donepezil.

The present patent application discloses novel compounds which display affinity and selectivity for the human sigma-1 receptor and for muscarinic subtype receptors, particularly the M1 and M2 subtypes. They are therefore expected to have utility on their own, or in combination with the aforementioned cholinesterase inhibitors, in the treatment of Alzheimer's disease and other non-AD dementias, Parkinson's and Huntington's diseases and ALS (amyotrophic lateral sclerosis, also referred to as Lou Gehrig's disease).

SUMMARY OF THE INVENTION

This invention is directed to compounds of the formula I:

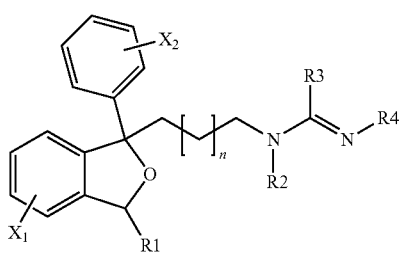

(I)

or the pharmaceutically acceptable salt(s) thereof, wherein:
$X_1$ is selected from the group consisting of H, $(C_1-C_4)$ alkyl, $(C_1-C_4)$-alkoxyl, $CF_3$, F, Cl, Br, I, CN.
$X_2$ is H, I, Br, Cl, or F;
n is zero, one or two;
$R_1$ is H, methyl, or dimethyl;
$R_2$ is H, $(C_1-C_6)$-alkyl;
R3 is H, $(C_1-C_6)$-alkyl, $(C_3-C_{12})$-cycloalkyl (optionally containing a O atom), aryl (optionally substituted by $X_3$), or $((C_1-C_6)$-alkyl)-aryl;
R4 is $(C_1-C_6)$-alkyl, aryl (optionally substituted by $X_4$); or R3 and R4 together with the carbon and nitrogen atoms to which they are attached form a 5-12 membered mono- or bi-cyclic ring system, (said ring system containing up to two additional heteroatoms selected from N, O or S, and said ring optionally substituted at available positions by one or more groups from a list which includes $(C_1-C_6)$-alkyl, $(C_1-C_6)$-alkoxyl and aryl) including, e.g., 4,5-dihydro-imidazol-2-yl; 1,3,4-oxadiazol-2-yl, 1,2,4-triazol-3-yl, tetrazole-5-yl, 3,4-dihydro-quinolin-2-yl; 3,4-dihydro-2H-pyrrol-5-yl; 2,3,4,5-tetrahydro-pyridin-6-yl; 1,2,3,6-tetrahydropyrazin-2-yl; 3,6-dihydro-2H-1,4-oxazin-5-yl; 1,2-dihydro-quinoxalin-3-yl; 4,5-dihydro-3H-2-benzazepin-1-yl; and 2,5-dihydro-1H-3-benzazepin-4-yl;

$X_3$ and $X_4$ are independently selected from the list consisting of: H, F, Cl, Br, I, CN, $(C_1-C_6)$-alkyl, $(C_3-C_{12})$-cycloalkyl, $CF_3$, $C_2F_5$, $OCF_3$, O—$(C_1-C_6)$-alkyl, O—$(C_1-C_6)$-alkoxyl, OH, $NO_2$, $NH_2$, NHR7 and NR7R8; wherein R7 and R8 are independently selected from the list including $(C_1-C_6)$-alkyl, $(C_3-C_{12})$-cycloalkyl and phenyl, or wherein R7 and R8 together with the N to which they are attached form a 4-12 membered mono- or bi-cyclic ring.

The invention is directed to a pharmaceutical composition for treating a disorder or condition in a mammal, including a human, from the list consisting of Alzheimer's disease (AD), other dementias, Parkinson's disease, Huntington's disease, and amyotrophic lateral sclerosis (i.e., ALS, Lou Gehrig's disease) which may be treated by administering to a mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the preceding paragraph, the method comprising administering to said mammal in need of such treatment an amount of a compound of formula I as described above that is effective in treating such disorder or condition.

The invention also relates to the use of a compound of the formula I, or a pharmaceutically acceptable salt thereof, in combination with a cholinesterase inhibitor selected from the group consisting of donepezil, galantamine, rivastigmine and memantine, for the treatment of a disorder or condition, the treatment of which can be effected or facilitated by administration of an effective amount of the combination to a mammal, including a human, in need of such treatment.

Preferred embodiments of the present invention include the compounds of formula I in which:
(A) R1 is hydrogen, R2 is methyl, R4 is hydrogen;
n is one; and
R3 is $(C_1-C_6)$ alkyl.
(B) R1 is hydrogen, R2 is methyl, R4 is hydrogen;
n is one; and
R3 is aryl (optionally substituted by $X_3$).
(C) R1 is hydrogen, R2 is methyl;
n is one; and
R3 and R4, taken together with the carbon and nitrogen atoms to which they are attached, respectively, form a 5-12 membered mono- or bi-cyclic ring system as previously defined.

The most preferred embodiment of the present invention includes the compounds of formula I in which:
(A) X1 is CN and X2 is fluoro, n is one;
R1 is hydrogen, R2 is methyl, R4 is hydrogen; and
R3 is phenyl.

(B) X1 is CN and X2 is fluoro, n is one;
R1 is hydrogen, R2 is methyl, R4 is hydrogen; and
R3 is ($C_1$-$C_6$) alkyl.

Preferred compounds of formula I in accordance with the present invention include the following:

1-(4-fluorophenyl)-1-{3-[methyl(3,4,5,6-tetrahydropyridin-2-yl)amino]propyl}-1,3-di-hydro-2-benzofuran-5-carbonitrile;

1-{3-[3,4-dihydro-2H-pyrrol-5-yl(methyl)amino]propyl}-1-(4-fluorophenyl)-1,3-di-hydro-2-benzofuran-5-carbonitrile;

1-{3-[3H-indol-2-yl(methyl)amino]propyl}-1-(4-fluorophenyl)-1,3-dihydro-2-benzo-furan-5-carbonitrile;

1-{3-[3,4-dihydroquinolin-2-yl(methyl)amino]propyl}-1-(4-fluorophenyl)-1,3-dihydro-2-benzofuran-5-carbonitrile;

1-{3-[3,4,4a,5,6,7,8,8a-octahydroquinolin-2-yl(methyl)amino]propyl}-1-(4-fluoro-phenyl)-1,3-dihydro-2-benzofuran-5-carbonitrile;

1-{3-[methyl(4-methyl-3,4,5,6-tetrahydropyrazin-2-yl)amino]propyl}-1-(4-fluorophenyl)-1,3-dihydro-2-benzofuran-5-carbonitrile;

1-{3-[5,6-dihydro-2H-1,4-oxazin-3-yl(methyl)amino]propyl}-1-(4-fluorophenyl)-1,3-di-hydro-2-benzofuran-5-carbonitrile;

1-{3-[5,6-dihydro-2H-1,4-thiazin-3-yl(methyl)amino]propyl}-1-(4-fluorophenyl)-1,3-di-hydro-2-benzofuran-5-carbonitrile;

1-{3-[methyl(2,3,6,7-tetrahydro-1,4-oxazepin-5-yl)amino]propyl}-1-(4-fluorophenyl)-1,3-dihydro-2-benzofuran-5-carbonitrile;

1-{3-[methyl(3,4,5,6-tetrahydro-2H-azepin-7-yl)amino]propyl}-1-(4-fluorophenyl)-1,3-dihydro-2-benzofuran-5-carbonitrile;

1-{3-[(2,2-dimethyl-3,4-dihydro-2H-pyrrol-5-yl)(methyl)amino]propyl}-1-(4-fluoro-phenyl)-1,3-dihydro-2-benzofuran-5-carbonitrile;

1-{3-[methyl(4H-1,2,3-triazol-5-yl)amino]propyl}-1-(4-fluorophenyl)-1,3-dihydro-2-benzofuran-5-carbonitrile;

N-3-(5-cyano-1-(4-fluorophenyl)-1,3-dihydro-2-benzofuran-1-yl)-propyl]-N-methyl-propanimidamide;

N-3-(5-cyano-1-(4-fluorophenyl)-1,3-dihydro-2-benzofuran-1-yl)-propyl]-N-methyl-cyclopropanecarboximidamide N-3-(5-cyano-1-(4-fluorophenyl)-1,3-dihydro-2-benzofuran-1-yl)-propyl]-N-methyl-cyclohexanecarboximidamide N-3-(5-cyano-1-(4-fluorophenyl)-1,3-dihydro-2-benzofuran-1-yl)-propyl]-N-methyl-tetrahydro-2H-pyran-4-carboximidamide;

N-3-(5-cyano-1-(4-fluorophenyl)-1,3-dihydro-2-benzofuran-1-yl)-propyl]-4-chloro-N-methylbenzenecarboximidamide;

N-3-(5-cyano-1-(4-fluorophenyl)-1,3-dihydro-2-benzofuran-1-yl)-propyl]-3,4-difluoro-N-methylbenzenecarboximidamide;

N-3-(5-cyano-1-(4-fluorophenyl)-1,3-dihydro-2-benzofuran-1-yl)-propyl]-4-methoxy-N-methylbenzenecarboximidamide;

N-3-(5-cyano-1-(4-fluorophenyl)-1,3-dihydro-2-benzofuran-1-yl)-propyl]-N-methyl-naphthalene-2-carboximidamide;

N-3-(5-cyano-1-(4-fluorophenyl)-1,3-dihydro-2-benzofuran-1-yl)-propyl]-N-methyl-naphthalene-1-carboximidamide;

(1Z)—N-3-(5-cyano-1-(4-fluorophenyl)-1,3-dihydro-2-benzofuran-1-yl)-propyl]-N,N'-dimethylethanimidamide;

(1E)-N-3-(5-cyano-1-(4-fluorophenyl)-1,3-dihydro-2-benzofuran-1-yl)-propyl]-N,N'-dimethylethanimidamide;

(1Z)—N-3-(5-cyano-1-(4-fluorophenyl)-1,3-dihydro-2-benzofuran-1-yl)-propyl]-N,N',2-trimethylpropanimidamide;

(1Z)—N-3-(5-cyano-1-(4-fluorophenyl)-1,3-dihydro-2-benzofuran-1-yl)-propyl]-N,N'-dimethyl-3-phenylpropanimidamide;

N-3-(5-cyano-1-(4-fluorophenyl)-1,3-dihydro-2-benzofuran-1-yl)-propyl]-N,N'-di-methyl-benzenecarboximidamide;

1-{-3-[4,5-dihydro-1H-3-benzazepin-2-yl-amino]propyl}-1-(4-fluorophenyl)-1,3-dihydro-2-benzofuran-5-carbonitrile;

N-{3-[5-cyano-1-(4-fluorophenyl)-1,3-dihydro-2-benzofuran-1-yl]propyl}-N-methyl-ethanimidamide;

N-{3-[5-cyano-1-(4-fluorophenyl)-1,3-dihydro-2-benzofuran-1-yl]propyl}-N-methyl-phenylmethanimidamide;

1-{3-[4,5-dihydro-3H-2-benzazepin-1-yl-amino]propyl}-1-(4-fluorophenyl)-1,3-dihydro-2-benzofuran-5-carbonitrile; and 1-{3-[4-methyl-3,4-dihydroquinoxalin-2-yl(methyl)amino]propyl}-1-(4-fluorophenyl)-1,3-dihydro-2-benzofuran-5-carbonitrile.

The most preferred compounds of the invention include:

1-(4-fluorophenyl)-1-{3-[methyl(3,4,5,6-tetrahydropyridin-2-yl)amino]propyl}-1,3-dihydro-2-benzo-furan-5-carbonitrile.

A preferred use for compounds of formula I is in the treatment of Alzheimer's disease. Other preferred uses for the compounds of formula I are in the treatment of non-Alzheimer's dementias.

DETAILED DESCRIPTION OF THE INVENTION

The compounds of formula I may be prepared as described in the following reaction schemes and discussions. Unless otherwise indicated, n, $X_1$, $X_2$, R1, R2, R3, R4, R5 and structural formulae II, III, IV and V in the reaction schemes and discussion that follow are as defined above.

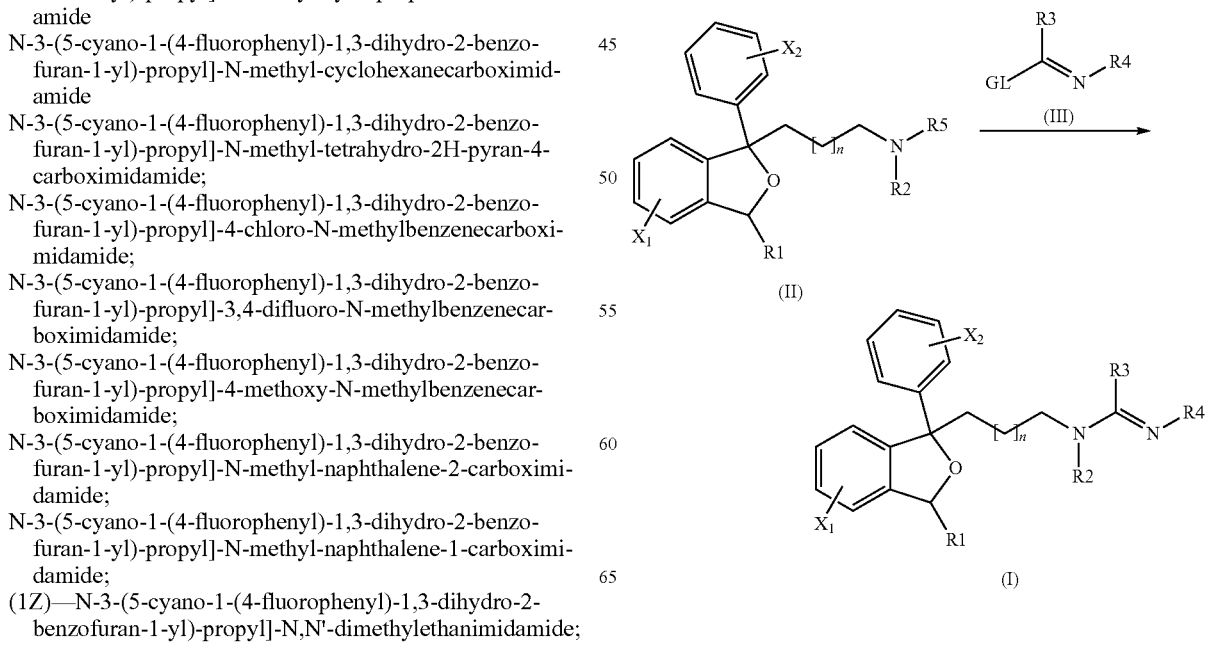

According to Scheme 1, compounds of the general formula II, wherein R5 is hydrogen, can be converted to the compounds of general formula I, by reaction with a compound of general formula III:

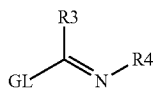

(III)

wherein R3 and R4 are as described above and GL is a leaving group, e.g., Cl, $OR_6$, $SR_6$, etc., and wherein R6 is $C_1$-$C_6$ alkyl. Formation of the resultant amidine group is well precedented in the chemical and patent literature. One excellent general reference, for example, is from R. L. Shriner and F. W. Neumann, "The Chemistry of the Amidines", 1944, 35:351-425. Other references include, for example, Moreau, et al, European Journal of Medicinal Chemistry, 1977, 12(4):365-369; Exner, et al, Journal of Molecular Structure, 1988, 178:147-159.

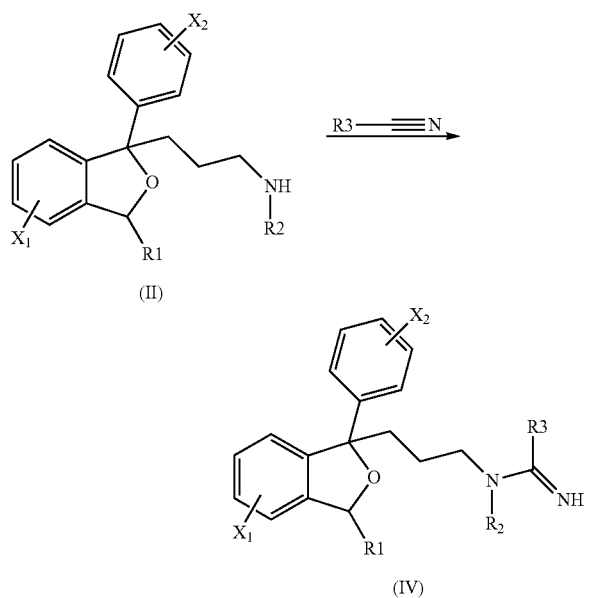

Scheme 2

An alternative method, as shown in Scheme 2, involves the reaction of a compound of general formula II, wherein R5 is hydrogen, with a nitrile of general formula V:

R3-C≡N     (V)

wherein R3 is as defined previously, to produce a compound of general formula IV (i.e., formula I wherein R4 is hydrogen). Using this procedure, $X_1$ is generally not equal to cyano (i.e., CN). Conditions for this procedure generally require the presence of an alcohol, preferably methanol or ethanol, and an anhydrous mineral acid, preferably hydrochloric acid, to be combined with the nitrile V and reacted within a temperature range of about 0° C. to about the boiling point of the alcohol employed, preferably at about 80° C. for ethanol, and at a pressure of about one to three atmospheres, preferably at atmospheric pressure, to generate an intermediate alkyl imidate. The intermediate imidate may then be isolated and purified, or reacted directly with the compound of general formula II in a reaction inert solvent such as toluene, 1,4-dioxane and the like, and stirred for up to 24 hr at a temperature in the range of about 0° C. to about 100° C. This process has been discussed in a number of literature sources, including those by Patai, "The Chemistry of Amidines and Imidates", Wiley, New York, 1975, pp. 385-489; R. Roger and D. Neilson, Chemical Reviews, 1961, 61(2): 179-211.

The starting materials for this process, compounds of the general formula II, are readily available using procedures described in the chemical and patent literature. For example, the compound of formula II, wherein n=1, R2=CH3, R5=CH3, R1=H, $X_2$ is 4-fluoro and the CN group is attached to the 5-position of the benzofuran ring has been commercially available as the antidepressant citalopram (in racemic form) and as the antidepressant escitalopram (as the single, (S)-isomer). Procedures for the syntheses of these compounds are also available in the literature (e.g., see M. Pitts, Tetrahedron, 2006, 62, 4705-4708; N. Periyandi, et al, PCT Int. Appl., (2006), WO-2006021971; T. Ikemoto and Y. Watanabe, PCT Int. Appl., (2005), WO-2005082842; H. Ahmadian and H. Petersen, PCT Int. Appl., (2003), WO-2003051861; H. Petersen, PCT Int. Appl. (2001), WO-2001068631; L. Dall'Asta, et al, PCT Int. Appl., (2000), WO-2000023431).

The starting material of general formula II, wherein R5 is hydrogen can be prepared from the preceding compounds by a mono-demethylation reaction. The process is also well precedented in the chemical literature and has been used to synthesize the major des-methyl metabolite of the above-mentioned citalopram and escitalopram. See, for example, C. Jin, et al (Synthetic Communications, 2007, 37, 901-908).

The compounds of the general formula III used in Scheme I above may be available commercially or can be prepared by methods disclosed in the chemical literature and known to one skilled in the art of organic chemistry. For example, see the Shriner paper above, and the specific references therein., For a more recent review of amidine chemistry, see M. S. dos Santos, et al, "Synthetic Approaches to Amidines", Quimica Nova, 2006, 29(6):1301-1306.

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl (tetralinyl), indenyl, and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-membered rings that contain from one to three heteroatoms independently selected from oxygen, nitrogen, and sulfur. Examples of preferred heteroaryl groups include benzo[b]thienyl, chromenyl, fury, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The compounds of formula I may also exist in the form of cis- or trans-isomers with respect to configuration on the furan ring of formula I. Such cis- and trans-isomers are also considered to be within the scope of the present invention, The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2$H, $^3$H, $^{11}$C, $^{13}$C, $^{14}$C, $^{13}$N, $^{15}$N, $^{17}$O, $^{18}$O, $^{35}$S, $^{31}$P, $^{32}$P, $^{31}$P, $^{18}$F and $^{37}$Cl, respectively. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof, and pharmaceutically acceptable salts of said compounds, or of said prodrugs which contain the aforementioned isotopes and/or other isotopes of other atoms are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above (e.g., HAT) in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by a compound, composition and method of this invention include: Alzheimer's disease (AD), Parkinson's disease (PD), Huntington's disease (HD), ALS and non-AD dementias.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:
  bm: broad multiplet (NMR)
  bs: broad singlet (NMR)
  d: doublet (NMR)
  dd: doublet of doublets (NMR)
  d.e.: diatomaceous earth, filtering agent
  calcd.: calculated value
  equiv: equivalent
  J: coupling constant (NMR)
  HPLC: high pressure liquid chromatography
  m: multiplet (NMR)
  min: minute(s)
  m/z: mass to charge ratio (mass spectroscopy)
  obsd: observed value
  Rf: retention factor (chromatography)
  RT: retention time (chromatography)
  rt: room temperature (typically 25° C.)
  s: singlet (NMR)
  t: triplet (NMR),
  T: temperature
  tlc: thin layer chromatography
  TFA: trifluoroacetic acid
  THF: tetrahydrofuran Solvents were purchased and used without purification. Yields were calculated for material judged homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton (i.e., $^1H$) NMR spectra are reported in parts per million (ppm) relative to the singlet of $CDCl_3$ at 7.24 ppm. Conditions for High Pressure Liquid Chromatography—Mass Spectrometry (HPLC-MS) Analysis:

Column: Zorbax RRHD Eclipse Plus (Agilent) $C_{18}$, 1.9 micron, 50 mm×2.1 mm

Eluent I.
A: Acetonitrile-$H_2O$=5:95, 20 mM $HCOONH_4$/$NH_4OH$ buffer, pH 7.4
B: Acetonitrile-$H_2O$=80:20, 20 mM $HCOONH_4$/$NH_4OH$ buffer, pH 7.4

Eluent II.
A: $H_2O$ with 0.1% TFA, pH 2.2
B: Acetonitrile with 0.1% TFA, pH 2.2

Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 μL
Detection wavelength: 220 nm Mass Spectrum (MS) conditions:
Measured Mass Range:100-750 Daltons
Scan Time: 0.2 s
Ion mode: ES±
Cone Voltage: 20 V
Capillary Voltage: 3 V
Source temp.: 140° C.
Desolvation temp.: 450° C.
Desolvation gas: 450 L/h
Cone gas: 60 L/h

EXPERIMENTAL SECTION

Preparation 1

1-[3-(methylamino)propyl]-1-(4-fluorophenyl)-1,3-dihydro-2-benzofuran-5-carbonitrile

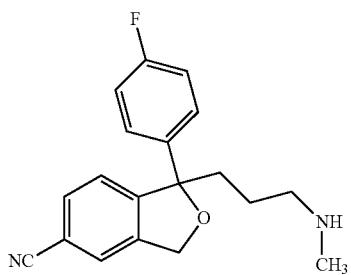 [SMILES: CNCCCC1(c2ccc(F)cc2)OCc2cc(C#N)ccc21]

The title compound was prepared according to the method of C. Jin, et al (*Synthetic Communications*, 2007, 37, 901-908). Thus, citalopram hydrobromide (5.5 g, 13.6 mmol) in 500 mL EtOAc was washed with dilute ammonium hydroxide (100 mL). The EtOAc layer was washed 3×100 mL saturated aqueous NaCl and dried with $MgSO_4$. The solvent was removed in vacuo and the residue was treated with 1-chlorethyl chloroformate (29.6 mL, 27.2 mmol), heated to 130° C. for 6 hr, cooled to rt and concentrated in vacuo. The residue was dissolved with 150 mL $CH_3OH$ and heated for 5 hr at 65° C. The solvents were then removed in vacuo. The crude product was dissolved in THF (50 mL) and 50 mL of 1N NaOH were added. The mixture was stirred at rt for an additional 14 hr, then extracted with EtOAc (3×50 mL). The extracts were washed with saturated NaCl (3×100 mL), dried with $Na_2SO_4$ and the solvents removed. Chromatography on silica gel, eluting with a gradient (100% $CH_2Cl_2$ to 50% $CH_3OH$: 50% $CH_2Cl_2$) gave the product as a clear oil, 3.102 g (74%).

Example 1

N-{3-[5-cyano-1-(4-fluorophenyl)-1,3-dihydro-2-benzofuran-1-yl]propyl}-N-methyl-ethanimidamide

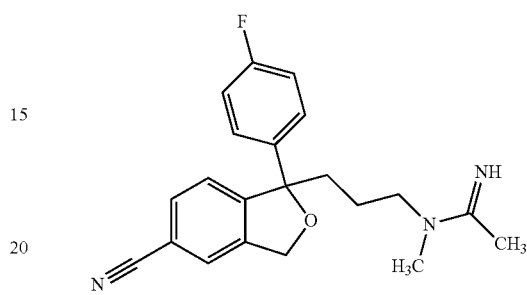

1-[3-(methylamino)propyl]-1-(4-fluorophenyl)-1,3-dihydro-2-benzofuran-5-carbonitrile (1.00 g, 3.22 mmol), the title compound from Preparation 1, and methyl ethanimidoate (0.283 g, 3.87 mmol, 1.2 equiv.) were dissolved in 1.9 mL of toluene and heated to 80° C. for 14 hr under $N_2$. The reaction was concentrated in vacuo to remove the toluene. The crude product was purified by liquid chromatography to give the title compound, 0.450 g (40%), as a light yellow semisolid. LC: 93.1%.

MS: calcd. for $C_{21}H_{22}FN_3O$: 351.43, obsd. 351.17 ($M^+$).
$^1$H-NMR (DMSO-$d_6$, 400 MHz, T=36° C.) δ 1.16-1.46 (dm, 2H), 1.90 (s, 3H, C—C$\underline{H}_3$), 2.15 (m, 2H), 2.70 (s, 3H, N—C$\underline{H}_3$), 3.18 (t, 2H), 5.18 (q, 2H), 6.30 (bs, 1H, =N$\underline{H}$), 7.15 (t, 2H), 7.58 (m, 2H), 7.76 (m, 3H).

Example 2

N-{3-[5-cyano-1-(4-fluorophenyl)-1,3-dihydro-2-benzofuran-1-yl]propyl}-N-methyl-phenylmethanimidamide

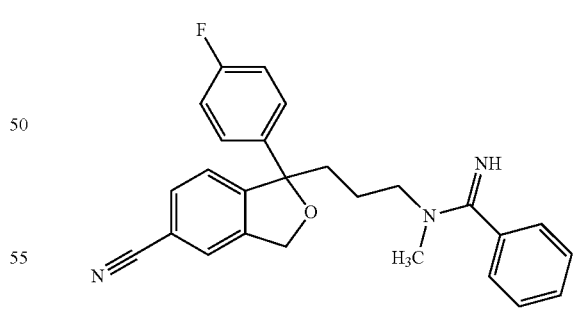

A mixture of 0.350 g (1.13 mmol) of 1-[3-(methylamino)propyl]-1-(4-fluorophenyl)-1,3-dihydro-2-benzofuran-5-carbonitrile (Preparation 1) and methyl benzenecarboximidoate hydrochloride (0.213 g, 1.24 mmol, 1.1 equiv.) in 0.7 mL of N-methyl-pyrrolidinone was treated with potassium carbonate (0.11 g, 0.79 mmol, 0.7 equiv.) and heated to 80° C. for 15 hr. The solvent was then removed and the crude product purified by column chromatography to give the title compound 0.096 g (19%) as a white solid. LC: 95.4%.

MS: calcd. for $C_{26}H_{24}FN_3O$: 413.50, obsd. 413.19 ($M^+$).
$^1$H-NMR (DMSO-$d_6$, 400 MHz, T=30° C.) δ 1.35 (m, 1H), 1.60 (dm, 1H), 2.0 (m, 1H), 2.30 (t, 1H), 2.85 (s, 1H), 3.15-3.25 (t, 2H), 3.55 (t, 1H), 5.05 (q, 1H), 5.20 (q, 1H), 7.15 (m, 2H), 7.37-7.90 (m, 10H), 8.9-9.4 (m, 2H).

Example 3

1-(4-fluorophenyl)-1-{3-[methyl(3,4,5,6-tetrahydro-pyridin-2-yl)amino]propyl}-1,3-dihydro-2-benzo-furan-5-carbonitrile

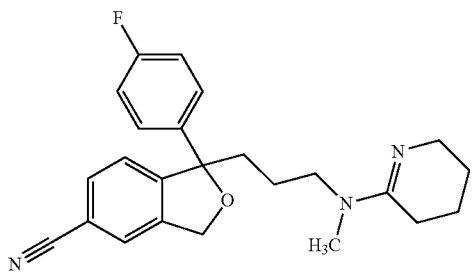 [SMILES: CN(CCCC1(c2ccc(F)cc2)OCc2cc(C#N)ccc21)C1=NCCCC1]

A mixture of 0.200 g (0.64 mmol) of 1-[3-(methylamino)propyl]-1-(4-fluorophenyl)-1,3-dihydro-2-benzofuran-5-carbonitrile (Preparation 1) and 6-methoxy-2,3,4,5-tetrahydropyridine (0.080 g, 0.71 mmol, 1.1 equiv.) was heated at 80° C. for 15 hr, cooled to rt and concentrated in vacuo to a gummy residue. The crude product was purified using column chromatography to give the title product as an off-white solid, 0.060 g (24%). LC: 97.1%.

MS: calcd. for $C_{24}H_{26}FN_3O$: 391.49, obsd. 391.21 ($M^+$).
$^1$H-NMR (DMSO-$d_6$, 400 MHz, T=30° C.) δ 1.23-1.52 (dm, 2H), 1.67 (m, 4H), 2.20 (m, 2H), 2.92 (s, 3H, —N—CH3), 3.20-3.45 (dt, 4H), 3.57 (s, 2H), 5.18 (q, 2H), 7.15 (t, 2H), 7.58 (m, 2H), 7.80 (m, 3H).

Determination of Pharmacological Activity

The compounds from the above Examples were tested for Sigma-1 and muscarinic M1-M5) activities. Ki determinations were generously provided by the National Institute of Mental Health's Psychoactive Drug Screening Program (PDSP), Contract #HHSN-271-2013-00017-C (NIMH PDSP). The NIMH PDSP is directed by Bryan L. Roth M D, PhD at the University of North Carolina at Chapel Hill and Project Officer Jamie Driscoll at NIMH, Bethesda Md., USA. Procedures employed by the PDSP are described in the NIMH PDSP Assay Protocol Book, Version II and follow published literature protocols.

| | Data | | | | | |
|---|---|---|---|---|---|---|
| | Ki (nM) | | | | | |
| Compound Example | Sigma1 | M1 | M2 | M3 | M4 | M5 |
| 3 | 230 | 1502 | 2571 | n/a | n/a | 1165 |
| ANAVEX 2-73 * | 860 | 3320 | 3970 | 5330 | 5190 | n/d | n/d—Not determined.
n/a—Not available.
Data from Poster, CNS Summit (2013)
[www.anavex.com/files/AVXL_PosterPresentation_11-13_CNS_Summit.pdf].

We claim:
1. A method of treating a disorder or condition, selected from the group consisting of Alzheimer's disease, Parkinson's disease, Huntington's disease, ALS and non-Alzheimer's dementias, comprising administering to a mammal in need of said treatment an effective amount of a compound of the formula I:

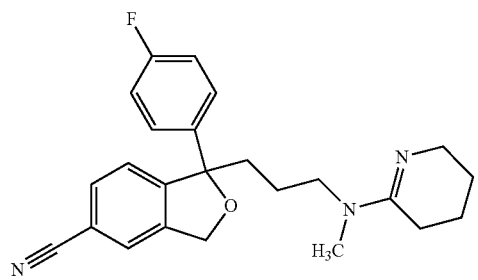

(I)

or the pharmaceutically acceptable salt(s) thereof.

* * * * *